(12) United States Patent
Brahmbhatt

(10) Patent No.: US 7,718,405 B2
(45) Date of Patent: May 18, 2010

(54) USE OF PURE OXYGEN IN VISCOUS FERMENTATION PROCESSES

(75) Inventor: Sudhir Brahmbhatt, Glencoe, MO (US)

(73) Assignee: American Air Liquide, Inc., Fremont, CA (US)

( * ) Notice: Subject to any disclaimer, the term of this patent is extended or adjusted under 35 U.S.C. 154(b) by 708 days.

(21) Appl. No.: 11/530,364

(22) Filed: Sep. 8, 2006

(65) Prior Publication Data

US 2007/0065927 A1     Mar. 22, 2007

Related U.S. Application Data

(60) Provisional application No. 60/718,462, filed on Sep. 19, 2005.

(51) Int. Cl.
*C12P 19/06*      (2006.01)

(52) U.S. Cl. ...................................... 435/104

(58) Field of Classification Search ........................ None
See application file for complete search history.

(56) References Cited

U.S. PATENT DOCUMENTS

| | | | |
|---|---|---|---|
| 4,041,180 A | 8/1977 | Wilson | |
| 4,169,010 A | 9/1979 | Marwil | |
| 4,649,114 A | 3/1987 | Miltenburger | |
| 4,692,408 A * | 9/1987 | Banks et al. | 435/104 |
| 4,808,534 A | 2/1989 | Schick et al. | |
| 5,198,362 A | 3/1993 | Forsyth | |
| 5,837,522 A | 11/1998 | Swain | |
| 5,972,661 A | 10/1999 | Kubera et al. | |
| 5,985,652 A | 11/1999 | Cheng | |
| 6,280,996 B1 | 8/2001 | Cheng | |
| 2003/0080446 A1 | 5/2003 | Cheng | |
| 2004/0023359 A1 | 2/2004 | Van Den Broecke | |
| 2004/0043444 A1 | 3/2004 | Van Hoek | |
| 2005/0067724 A1 | 3/2005 | Cheng | |
| 2005/0181499 A1 | 8/2005 | Brahmbhatt | |

FOREIGN PATENT DOCUMENTS

| | | |
|---|---|---|
| EP | 0341878 B1 | 11/1989 |
| EP | 0317854 B1 | 10/1993 |
| EP | 0901812 A1 | 3/1999 |
| GB | 1035551 | 7/1966 |
| JP | 59146584 | 8/1984 |
| JP | 63156514 | 6/1988 |
| JP | 63216467 | 9/1988 |

OTHER PUBLICATIONS

PCT Int'l Search Report, Nov. 28, 2006, PCT/IB2006/002504.
Mehmet D. Oner, Sami Eren, Senol Ibanoglu, Growth and Energetic Parameters of Microbial Xanthan Gum Production with Xanthomonas Campestris, Journal of Engineering and Enviromental Sciences, 1995, 239-245, Gaziantep-Turkey.
Meenal S. Puthli, Virendra K. Rathod, Aniruddha B. Pandit, Gas-Liquid Mass Transfer Studies with Triple Impeller System on a Laboratory Scale Bioreactor Biochemical Engineering Journal, 2005, 25-30, 23, Matunga Mumbai India.
Hossein Nikakhtari and Gordon A. Hill, Enhanced Oxygen Mass Transfer in an External Loop Airlift Bioreactor Using a Packed Bed, Ind. Eng. Chem. Res., 2005, 1067-1072, 44, Tabriz Iran.
Yinliang Chen, Julia Cino, Glen Hart, David Freeman, Christopher White, Elizabeth A. Komives, High Protein Expression in Fermentation of Recombinant Pichia Pastoris by a Fed-Batch Process, Process BioChemistry, 1997, 107-111, 32, 2, Great Britain.
Jae Gu Pan, Joon Shick Rhee, Jean M. Lebeault, Physiological Constraints in Increasing Biomass Concentration of *Escherichia coli* B in Fed-Batch Culture, Biotechnology Letters, 1987, 89-94, 9, 2, Seoul Korea.

* cited by examiner

*Primary Examiner*—Jon P Weber
*Assistant Examiner*—Satyendra K Singh
(74) *Attorney, Agent, or Firm*—Christopher J. Cronin

(57) ABSTRACT

A fermentation process uses substantially pure oxygen as the sole gas introduced into a fermentation vessel while fermentation reactions are active. The oxygen is introduced at multiple locations along the height of the vessel, and is preferably introduced in the vicinity of the blades of an impeller. The invention enhances the rate at which oxygen can be transferred to the fermentation medium, and is especially useful for fermentation media which become very viscous as the process continues. The invention can be used in the manufacture of viscous products such as xanthan gum, or other products having viscosities greater than about 100 cp.

6 Claims, 1 Drawing Sheet

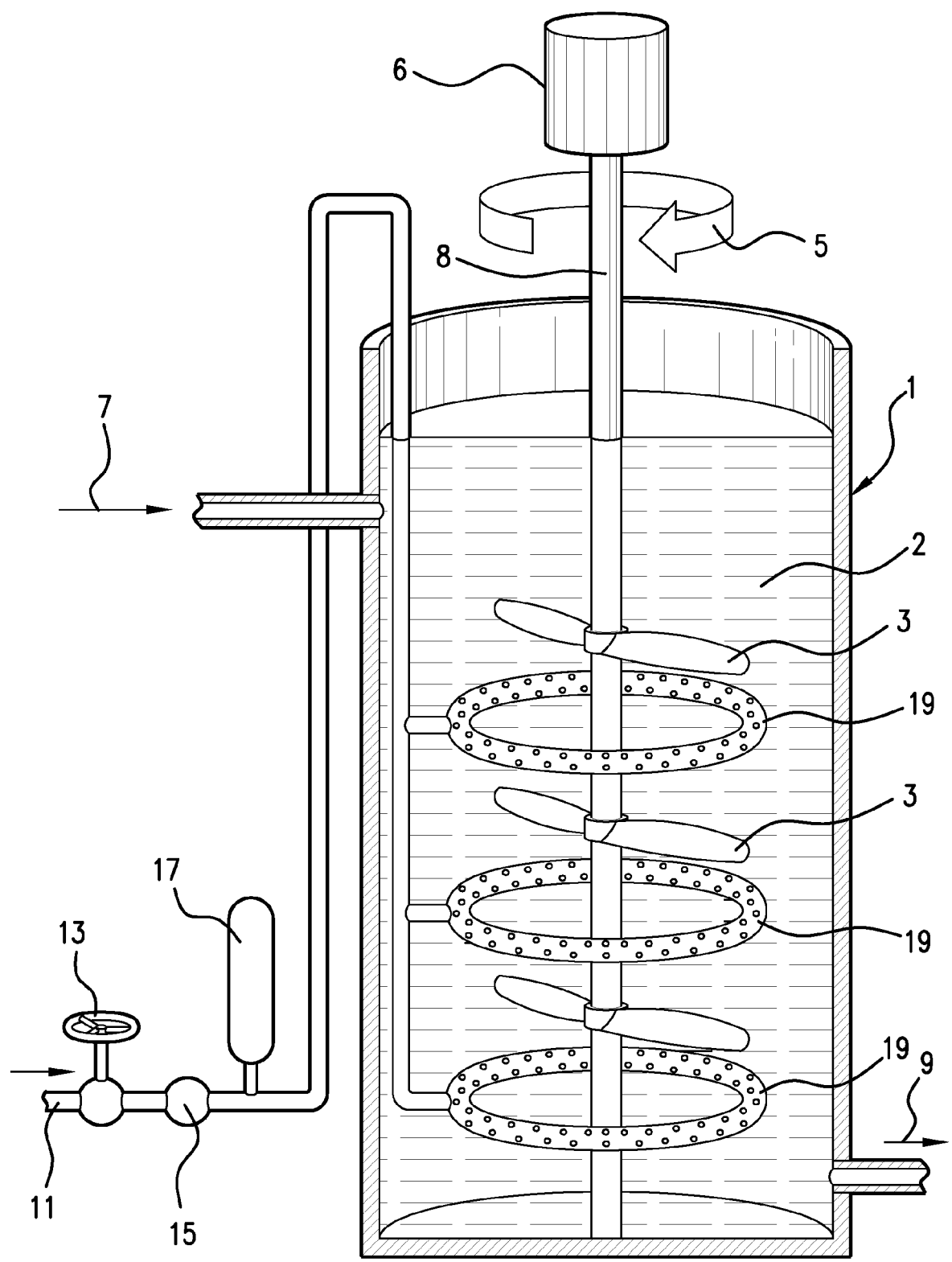

USE OF PURE OXYGEN IN VISCOUS FERMENTATION PROCESSES

CROSS-REFERENCE TO PRIOR APPLICATION

Priority is claimed from U.S. provisional patent application Ser. No. 60/718,462, filed Sep. 19, 2005, the entire disclosure of which is incorporated by reference herein.

BACKGROUND OF THE INVENTION

The present invention relates to aerobic fermentation processes, and provides a method and apparatus which is especially suitable in cases where the fermentation products are highly viscous.

A typical fermentation process includes four phases, namely the lag phase, the growth phase, the stationary phase, and the death phase. The lag phase is essentially a preparatory phase, while the remaining phases are operational phases in which the actual fermentation process is conducted.

The operational phases of an aerobic fermentation process require a constant supply of oxygen. Without oxygen, the organisms responsible for the fermentation process may die, or they may produce an undesirable product. Oxygen must be continuously transferred into the fermentation medium, in order for the fermentation process to continue, and for the microbes in the fermentation medium to produce a desired product.

In certain applications, the fermentation products become very viscous. For example, in the manufacture of xanthan gum, using *Xanthomonas Campestris*, the fermentation broth begins with a viscosity comparable to that of water, of the order of 1 centipoise (cp). But as the process continues, and the concentration of the product xanthan gum approaches 2-4%, the viscosity of the fermentation medium may reach a level of the order of 20,000 cp. By comparison, a typical value for the viscosity of oil is in the range of about 100-300 cp.

The production of a highly viscous fermentation product is made difficult by the fact that the viscosity of the medium inhibits the transfer of oxygen to the organisms in the medium. In the prior art, the oxygen has been derived from a stream of air which is pumped into the fermentation vessel, the air being mixed into the medium by mechanical agitators. But the more product that is made, the more viscous the medium becomes, and the greater the difficulty in transferring the necessary oxygen into the medium. The fermentation process is therefore limited by the rate of oxygen transfer. The process is self-limiting, insofar as the very success of the fermentation process will cause the process to slow down, or even cease, due to lack of oxygen. When the fermentation product is highly viscous, the oxygen transfer rate becomes the most important limiting factor to the productivity of the fermentation process.

In the prior art, efforts have been made to solve the above problem by increasing the flow of air into the fermentation vessel, and increasing the agitation speed. Increasing agitation speed produces more turbulence in the fermentation medium, and the turbulence tends to enhance the mixing of air into the medium, thereby increasing the oxygen transfer rate. But experiments have shown that, while increasing the agitation speed does improve the oxygen transfer rate, the improvement is only marginal. The exact amount of improvement obtained by increasing agitation speed depends on the geometry of the vessel and the configuration of the agitator blades. Moreover, increasing the agitation speed consumes considerable energy, and it turns out that the benefit in increased oxygen transfer usually does not outweigh the additional energy cost.

Likewise, increasing the flow rate of the air introduces new problems, such as impeller flooding, foaming of product in the fermentation medium, and reduction in the efficiency of dissolution of oxygen into the medium, due to a reduced residence time of air in the vessel.

Still another way to address the problem is to replace the fermentation vessel with a larger one. This approach would tend to delay the onset of oxygen starvation, because of the larger volume of the fermentation medium. But this approach is expensive, and it only postpones, and does not solve, the fundamental problem of oxygen transfer through a viscous medium.

The present invention provides a fermentation process and method which solves the problem described above, and which provides an economical means for making a highly viscous fermentation product.

SUMMARY OF THE INVENTION

The present invention includes a fermentation method and apparatus, especially suitable for use with a fermentation medium which becomes highly viscous. The fermentation apparatus includes a vessel having an agitator. According to the present invention, substantially pure oxygen is introduced into the vessel, and is the only gas introduced into the vessel while the fermentation is proceeding. The oxygen is introduced at a plurality of locations along the height of the vessel, and preferably is introduced in the vicinity of the blades of the agitator. Introduction of oxygen in this manner improves the distribution of oxygen to various locations within the vessel.

The oxygen injectors may include perforated pipes, each shaped in the form of a toroid. The perforations in the pipes preferably have a diameter smaller than comparable perforations used, in the prior art, for delivery of air. The diameter of the perforations may be in a range of about 0.0625-0.5 inches, or even smaller. In general, the smaller the perforations, the smaller the size of the oxygen bubbles released into the fermentation medium.

To remove debris that might clog the holes in the injectors, the injectors may be periodically purged with air. However, this air is used only during maintenance, and not when the fermentation process is operating.

The oxygen used in the present invention is produced outside the fermentation vessel, and is introduced to the vessel as a gas. Unlike some systems of the prior art, the fermentation medium is not removed from the vessel for oxygenation; the only time the medium is removed is when the fermentation process is complete. The present invention is therefore more simple in construction, and more economical to build, than many systems of the prior art.

The invention therefore has the primary object of providing a method and apparatus for operating a fermentation process, where the fermentation medium becomes highly viscous.

The invention has the further object of enhancing the efficiency of a fermentation process, for viscous fermentation media.

The invention has the further object of enhancing the rate of oxygen transfer into a viscous fermentation medium.

The invention has the further object of providing a fermentation method and apparatus as described above, wherein the invention can be conveniently practiced by retrofitting an existing fermentation vessel.

The invention has the further object of improving the throughput of a fermentation process involving a highly viscous product, of the order of 100 cp or higher.

The invention has the further object of providing a fermentation system and method for use with viscous media, wherein the system is economical to build and operate.

The reader skilled in the art will recognize other objects and advantages of the invention, from a reading of the following brief description of the drawing, the detailed description of the invention, and the appended claims.

BRIEF DESCRIPTION OF THE DRAWING

The FIGURE provides a schematic diagram of a fermentation system made according to the present invention.

DETAILED DESCRIPTION OF THE INVENTION

The rate of oxygen transfer into a fermentation medium can be described by the following equation:

$$OTR = dC_L/dt = K_L a(C^* - C_L)$$

where

OTR=oxygen transfer rate, $C_L$=concentration of dissolved oxygen in the fermentation broth, $C^*$=dissolved oxygen concentration at saturation, and $K_L a$=mass transfer coefficient times the gas-liquid interface area per liquid volume, also known as the volumetric transfer coefficient.

The quantity $C^*$ is thus a value of maximum concentration, and is a constant. The quantity $(C^* - C_L)$ is known as the concentration gradient, i.e. the difference between actual concentration and maximum possible concentration. Thus, the oxygen transfer rate is proportional to concentration gradient.

The coefficient $K_L a$ varies with the geometry of the fermenter, with the rotation speed of the agitator, and with the viscosity of the medium. Information about this coefficient is given in Y. M. Lo et al, Bioprocess and Bio Systems Engineering 24 (2001) pages 187-193. In general, for a fermentation process which starts with a medium having a viscosity of the order of 1 cp, and ends with a viscosity of the order of 20,000 cp, the value of $K_L a$ might fall by 85% or more, and the concentration gradient might fall by about 25%.

The present invention includes directing a stream of substantially pure oxygen into the fermentation vessel. Unlike fermentation systems of the prior art, no air is introduced into the vessel to support the fermentation process. The oxygen is the only gas which is introduced into the vessel while fermentation is in progress.

When air is bubbled through water, under ideal conditions, the water will hold dissolved oxygen in a concentration of about 6-8 ppm. When pure oxygen is used instead of air, the level of dissolved oxygen will increase by as much as five times, or up to about 40 ppm or more. The same applies when the medium is more viscous than water. Thus, when pure oxygen is used, the dissolved oxygen concentration at saturation ($C^*$) is much higher than the value for air. In other words, by using pure oxygen instead of air, one immediately boosts the concentration gradient $C^* - C_L$. Since the oxygen transfer rate is proportional to the concentration gradient, the use of pure oxygen, instead of air, substantially increases the oxygen transfer rate.

Another important aspect of the invention is that the oxygen is introduced to the vessel at multiple locations. More specifically, the oxygen should be introduced at a variety of positions along the height of the vessel. The reason for this arrangement is to promote proper diffusion of pure oxygen through the entire fermentation medium. Such diffusion is especially important where, as here, the medium becomes extremely viscous.

The FIGURE shows a fermentation vessel made according to the present invention. Vessel 1 holds a fermentation medium 2, the medium being agitated by impellers 3, connected to shaft 8, the shaft being rotated by motor 6, as indicated by arrow 5. Water for cooling is introduced as indicated by arrow 7, and withdrawn from the vessel as indicated by arrow 9. Oxygen enters the system through conduit 11, passing through shut-off valve 13 and check valve 15. Flow switch 17 is used to indicate the amount of gas flow, and to switch off the flow if it is necessary to shut down the process. A more sophisticated control means could be provided to control the flow of oxygen into the vessel. For example, the concentration of oxygen in the head space of the vessel can be measured, and the flow of oxygen into the vessel can be controlled in response to the measured head space oxygen concentration.

In the embodiment shown, the oxygen entering the vessel is distributed among three injectors 19, each injector being positioned at a different vertical location within the vessel. In a preferred embodiment, each injector comprises a toroid made of perforated pipe, wherein the oxygen can flow through the pipe and exit, through the perforations, into the vessel. Other constructions for the injectors could be used instead of what is shown in the FIGURE.

Three important criteria in designing the fermentation system of the present invention include the location of the injectors, the size of the injector holes, and the number of injectors. All of these parameters are chosen according to the type of fermentation medium, the characteristics of the medium (such as viscosity, density, and surface tension), and the type of agitator, including the impeller design and the number of impellers.

Each injector is preferably located as close to an impeller as possible. This positioning is necessary to maximize the shearing effect, wherein the impeller blades shear the oxygen bubbles, emerging from the injector, to create even finer bubbles.

In general, the injector holes, through which pure oxygen passes into the fermentation vessel, should be smaller than comparable holes of prior art injectors which are used to deliver air. For example, if the diameter of an injector hole used in a particular prior art fermenter is 0.5 inches, the diameter of the hole used in the present invention might be 0.25 inches, or even 0.125 inches, or less. The reason for using relatively small holes is to reduce the size of the oxygen bubbles created in the medium, and to benefit from the increased residence time of the bubbles in the medium.

The nature of the medium affects the choice of size of the injector holes. The object is to increase the retention time for oxygen bubbles in the medium, thereby allowing more oxygen to become dissolved in the medium.

In one example, wherein the fermenter is equipped with a "one-flight" impeller, i.e. an agitator having one pair of blades, the size of the injector hole could be two hole sizes smaller than that of the hole used to deliver air in the prior art. For example, if the prior art hole had a diameter of 0.5 inches, the hole size used in the present invention might be 0.125 inches.

The number of injectors used depends on how well the medium needs to be mixed, and on how many impeller flights are provided. For a three-flight agitator, three injectors at different heights are desirable. However, if the top oxygen injector causes too much oxygen to appear in the exhaust, it may be desirable to disable the top injector.

In the prior art, it has been taught to use large bubbles of air, because the large bubbles help to drive off carbon dioxide, and also because large bubbles imply large injector holes, which are less likely to become clogged with debris. The present invention represents a departure from this prior art teaching, insofar as smaller injector hole sizes are preferred. In the present invention, the turbulence induced by the impellers drives off the carbon dioxide. With respect to possible clogging of the injector holes, the injectors can be periodically purged with air, or another suitable gas, when the fermentation vessel is undergoing maintenance.

Note that the present invention does not use the above-mentioned air while a fermentation process is operating within the vessel, but only while the vessel is being maintained, and not being used for fermentation. Thus, substantially pure oxygen is still the only gas introduced into the vessel for promoting fermentation, in the present invention. While the fermentation process is in operation, the oxygen is introduced into the vessel as a continuous stream.

The purge air, used to prevent the injector from becoming clogged, would be used only for a relatively small amount of time. Air would be preferable for the purge, because it is less expensive than oxygen, and will serve to unclog the holes just as well as a more expensive gas.

In the present invention, the oxygen injector holes will usually have a diameter in the range of about 0.0625-0.5 inches. The holes might even be smaller, in certain applications. The above-cited range is given by way of example only, and is not intended to limit the scope of the invention.

In summary, the major features of the present invention include 1) the use of substantially pure oxygen, and no air, supplied as a continuous stream while the fermentation process is operating, 2) the injection of substantially pure oxygen at different heights within the fermentation vessel, and 3) the choice of bubble size and the physical location of the injectors with respect to the agitation system in the fermenter.

In the present invention, the oxygen introduced into the fermentation vessel is produced outside the vessel, and is introduced only in gaseous form. Unlike various fermentation systems of the prior art, in which some or all of the fermentation medium is removed from the vessel, possibly oxygenated, and then returned to the vessel, the fermentation medium in the present invention is never removed for oxygenation and recycling. In the present system, the fermentation medium is removed from the vessel only when the fermentation process is completed. The oxygen is supplied to the vessel as a gas, and not as a liquid-gas mixture.

Existing fermenters can be easily retrofitted to work according to the present invention. Such prior art fermenters typically include an air conduit, disposed at or near the bottom of the vessel, wherein air can be bubbled through holes in the conduit and into the vessel. Retrofitting a prior art fermenter simply requires the installation of an inlet conduit and a plurality of injectors, disposed at different vertical locations, within the vessel. The air line could then be closed off or otherwise temporarily or permanently disabled, as it would not be used to supply oxygen for fermentation, but it might be used for other purposes.

Because the present invention increases the concentration gradient, the pure oxygen transfers quickly to the areas in the fermentation vessel where the concentration is lower, and will quickly become available to the microorganisms. The present invention therefore overcomes the limitation in oxygen availability. Also, by introducing the oxygen at different vertical locations within the vessel, the need for agitation can be further reduced to the minimum level needed to strip carbon dioxide from the medium.

In the lag phase of a fermentation process, the requirement for oxygen is minimal. During this phase, the microbes adjust to their new environment from a seed fermentation step, before the start of regular fermentation. In the growth phase, the microbes start to consume oxygen, and at this point, the oxygen requirement increases. Because very little oxygen is required during the lag phase, it is possible to use air, instead of oxygen, to save money during this step. As explained above, during the lag phase, significant fermentation is not really occurring, as the fermentation does not truly begin until the growth phase. Thus, it does not contradict the present invention to use air, instead of pure oxygen, during the lag phase only. However, it is also possible to use pure oxygen during all phases, including the lag phase, if desired.

The present invention is especially useful in making products such as xanthan gum, which has a viscosity of the order of 20,000 cp. In general, the invention is useful in making products having viscosities of 100 cp and above.

The present invention therefore overcomes the limitations of the prior art, and provides a process which allows higher productivity, at the expense of a relatively modest capital investment. By using oxygen instead of air, one can increase the oxygen transfer rate without increasing the energy consumption of the agitator. It may even be possible to reduce the agitator speed, while still enjoying improved oxygen transfer rates.

The substantially pure oxygen used in the present invention could come from oxygen which is stored in liquid form, and vaporized immediately before use. Alternatively, it could be stored as a compressed gas, produced previously by cryogenic means, and released, when needed, from a cylinder or other container. In these cases, where the oxygen is generated by vaporizing a cryogenic liquid, or by a conventional distillation process, the oxygen may be at least about 99% pure.

The oxygen could instead be produced by non-cryogenic means, such as through the use of an air-separation membrane, or a pressure swing adsorption (PSA) unit. In these cases, the purity of the oxygen is likely to be in the range of about 80-95%.

In the present invention, the term "substantially pure" is intended to include all of the above alternatives.

The invention can be modified in various ways. The size of the vessel, the configuration of the conduits, and the choice of valves can all be varied. The number of injectors can be changed. These and other modifications, which will be apparent to those skilled in the art, should be considered within the spirit and scope of the following claims.

What is claimed is:

1. In a method for making a product by fermentation including a lag phase and a growth phase, the method including agitating a fermentation medium in a vessel, while introducing substantially pure oxygen into the medium, the vessel having a height, wherein the process is performed with a fermentation product which reaches a viscosity greater than about 100 cp, the improvement wherein:
   the substantially pure oxygen is introduced at a plurality of locations in the medium along the height of the vessel; and wherein the substantially pure oxygen is the only gas which is introduced into the vessel during the growth phase.

2. The improvement of claim 1, wherein agitating is performed by at least one impeller, and wherein the oxygen is introduced in a vicinity of the impeller.

3. The improvement of claim 2, wherein the oxygen is introduced through injector holes which are selected to have a diameter in a range of about 0.0625-0.5 inches.

4. The improvement of claim 1, wherein the process is performed with a fermentation product which reaches a viscosity in the area of about 20,000 cp.

5. The improvement of claim 1, wherein the fermentation medium is selected to contain *Xanthomonas campestris*, and wherein the fermentation product is xanthan gum.

6. The improvement of claim 1, wherein the oxygen is produced outside the vessel and is introduced in gaseous form into the vessel, and wherein the method is operated without removing all or part of the fermentation medium for oxygenation.

* * * * *